(12) United States Patent
Ishihara et al.

(10) Patent No.: US 11,236,062 B2
(45) Date of Patent: Feb. 1, 2022

(54) METHOD FOR PRODUCING 5-(BROMOMETHYL)-1-BENZOTHIOPHENE

(71) Applicants: FUJIFILM Toyama Chemical Co., Ltd., Chuo-ku (JP); FUJIFILM CORPORATION, Minato-ku (JP)

(72) Inventors: Kentaro Ishihara, Toyama (JP); Tsuyoshi Arai, Kaisei (JP)

(73) Assignees: FUJIFILM Toyama Chemical Co., Ltd., Chuo-ku (JP); FUJIFILM CORPORATION, Minato-ku (JP)

( * ) Notice: Subject to any disclaimer, the term of this patent is extended or adjusted under 35 U.S.C. 154(b) by 0 days.

(21) Appl. No.: 16/089,633

(22) PCT Filed: Mar. 30, 2017

(86) PCT No.: PCT/JP2017/013206
§ 371 (c)(1),
(2) Date: Sep. 28, 2018

(87) PCT Pub. No.: WO2017/170850
PCT Pub. Date: Oct. 5, 2017

(65) Prior Publication Data
US 2019/0119242 A1   Apr. 25, 2019

(30) Foreign Application Priority Data

Mar. 31, 2016  (JP) .............................. JP2016-071574

(51) Int. Cl.
*C07D 333/54* (2006.01)
*B01J 19/12* (2006.01)

(52) U.S. Cl.
CPC .......... *C07D 333/54* (2013.01); *B01J 19/123* (2013.01); *B01J 19/127* (2013.01); *B01J 2219/0877* (2013.01); *B01J 2219/1203* (2013.01)

(58) Field of Classification Search
CPC ..... C07D 333/54; B01J 19/127; B01J 19/123; B01J 2219/1203; B01J 2219/0877
(Continued)

(56) References Cited

U.S. PATENT DOCUMENTS 3,354,066 A     11/1967  Huyser et al.
3,567,921 A *   3/1971   Holiday ................. B01J 19/123
                                                        250/428
(Continued)

FOREIGN PATENT DOCUMENTS

EP        0 914 357 B1     9/2002
EP        1 032 557 B1     9/2003
(Continued)

OTHER PUBLICATIONS

Brabander, "Synthesis of Benzo [ b] thiophene-3-carboxaldehydes and -3-Carboxylic Acids by Light Catalyzed NBS Bromination of 3-Methylbenzo[b] thiophenes," J. Heterocyclic Chem. 1973, vol. 10, pp. 127-129 (Year: 1973).*

(Continued)

*Primary Examiner* — Nicholas A Smith
(74) *Attorney, Agent, or Firm* — Oblon, McClelland, Maier & Neustadt, L.L.P.

(57) ABSTRACT

Provided is a method for industrially producing 5-(bromomethyl)-1-benzothiophene. The production method according to the present invention comprises: (1) a step for introducing 5-methyl-1-benzothiophene, a brominating agent, and a solvent into a reactor; (2) a step for emitting light having a wavelength range of 200-780 nm inside the reactor; and (3) a step for recovering 5-(bromomethyl)-1-benzothiophene from the reactor.

5 Claims, 1 Drawing Sheet

(58) Field of Classification Search
USPC .................................................. 204/157.7
See application file for complete search history.

(56) References Cited

U.S. PATENT DOCUMENTS

| | | | | |
|---|---|---|---|---|
| 3,947,336 | A * | 3/1976 | Clarke | C07D 307/34 204/157.69 |
| 4,046,656 | A * | 9/1977 | Davis et al. | C07B 39/00 204/157.99 |
| 4,235,685 | A * | 11/1980 | Bauer | B01J 19/128 204/157.69 |
| 5,068,359 | A * | 11/1991 | Huxley | A01N 43/36 549/469 |
| 5,670,582 | A | 9/1997 | Chung et al. | |
| 5,750,728 | A * | 5/1998 | Wagner | C07B 39/00 549/57 |
| 6,214,999 | B1 | 4/2001 | Biard et al. | |
| 2003/0134880 | A1 | 7/2003 | Bruton et al. | |
| 2003/0176490 | A1* | 9/2003 | Saitoh | C07D 333/64 514/443 |
| 2003/0195191 | A1 | 10/2003 | Burton et al. | |
| 2005/0239780 | A1 | 10/2005 | Suga et al. | |
| 2007/0093526 | A1 | 4/2007 | Boulet et al. | |
| 2009/0069576 | A1 | 3/2009 | Saitoh et al. | |
| 2010/0279983 | A1 | 11/2010 | Dininno et al. | |
| 2015/0376502 | A1 | 12/2015 | Tanaka et al. | |

FOREIGN PATENT DOCUMENTS

| | | | |
|---|---|---|---|
| EP | 1 367 058 A1 | 12/2003 | |
| EP | 2 957 554 A1 | 12/2015 | |
| JP | 62138489 A * | 6/1987 | |
| JP | 2000-515193 A | 11/2000 | |
| JP | 2001-523658 A | 11/2001 | |
| JP | 2003-523994 A | 8/2003 | |
| JP | 2003-532727 A | 11/2003 | |
| JP | 2006-111553 A | 4/2006 | |
| JP | 2013-121923 A | 6/2013 | |
| JP | WO2014/125911 A1 | 8/2014 | |
| RU | 2 473 586 C1 | 1/2013 | |
| WO | WO 01/62715 A1 | 8/2001 | |
| WO | WO 01/85721 A1 | 11/2001 | |
| WO | WO 03/101983 A1 | 12/2003 | |
| WO | WO 2005/092885 A1 | 10/2005 | |
| WO | WO 2006/104088 A1 | 10/2006 | |
| WO | WO 2008/073142 A2 | 6/2008 | |

OTHER PUBLICATIONS

Brabander, "The Synthesis of Benzo [b] thiophene-3-carboxaldehydes and -3-carboxylic acids by Light Catalyzed NBS Bromination of 3-Methylbenzo [b] thiophenes," J. Heterocycl. Chem, vol. 10, issue 1, pp. 127-129 (1973) (Year: 1973).*

International Search Report dated Jun. 6, 2017, in PCT/JP2017/013206, filed Mar. 30, 2017.

Meyer, M. et al., "Structure-Activity Studies for a Novel Series of N-(Arylethyl)-N-(1,2,3,4-tetrahydronaphthalen-1-ylmethyl)-N-methylamines Possessing Dual 5-HT Uptake Inhibiting and $\alpha_2$-Antagonistic Activities", Journal of Medicinal Chemistry, vol. 40, No. 7, Mar. 28, 1997,pp. 1049-1062.

Russian Office Action and Search Report dated May 27, 2020, in Patent Application No. 2018138147, 11 pages (with English translation).

Extended European Search Report dated Aug. 9, 2019 in Patent Application No. 17775384.5, 6 pages Peter Nussbaumer, et al., "Synthesis and Structure-Activity Relationship of Benzo[b]thienylallylamlne Antimycotics" Journal of Medicinal Chemistry, vol. 34, No. 1, XP002792910, Jan. 1, 1991, pp. 65-73.

* cited by examiner

METHOD FOR PRODUCING 5-(BROMOMETHYL)-1-BENZOTHIOPHENE

TECHNICAL FIELD

The present invention relates to a method for producing 5-bromomethyl-1-benzothiophene which is useful as a production intermediate for pharmaceuticals.

BACKGROUND ART 1-(3-(2-(1-benzothiophen-5-yl)ethoxy)propyl)azetidin-3-ol is a compound useful as a therapeutic agent for diseases of the central and peripheral nerves. This compound is produced, for example, from 1-benzothiophene-5-acetic acid (Patent Document 1). Then, 1-benzothiophene-5-acetic acid is produced, for example, from 5-bromomethyl-1-benzothiophene (hereinafter sometimes referred to as "Compound A") (Non Patent Document 1).

Compound A is a compound useful as an intermediate for pharmaceuticals.

On the other hand, as a method for producing Compound A, the method involving the bromination of 5-methyl-1-benzothiophene (hereinafter sometimes referred to as "Compound B") has been known (Patent Documents 2 to 4).

PRIOR ART DOCUMENTS

Patent Documents

Patent Document 1
International Publication No. WO2006/104088 pamphlet
Patent Document 2
International Publication No. WO2008/073142 pamphlet
Patent Document 3
JP 2006-111553 A
Patent Document 4
International Publication No. WO2005/092885 pamphlet

Non Patent Document

Non Patent Document 1
Journal of Medicinal Chemistry (J. Med. Chem.), 1997, Vol. 40, pp. 1049-1062

SUMMARY OF INVENTION

Technical Problem

The methods for producing Compound A described in Patent Documents 2 to 4 have the following drawbacks: (1) carbon tetrachloride is toxic; (2) thus, the use of carbon tetrachloride is prohibited; (3) 5-dibromomethyl-1-benzothiophene is produced as a by-product; (4) therefore, a complicated purification step is necessary.

An object of the present invention is to provide a method for industrially producing Compound A, which is simple and has no influence on human bodies.

Solution to Problem

Under such circumstances, the present inventors have conducted intensive researches, and consequently have found that Compound A is produced with simple operation by converting a conventional batch-type reaction to a flow-type reaction in the bromination step of Compound B, and completed the present invention.

The present invention provides the following.

[1] A method for producing 5-bromomethyl-1-benzothiophene comprising the steps of: (1) introducing 5-methyl-1-benzothiophene, a brominating agent and a solvent into a reactor; (2) irradiating the interior of the reactor with light having a wavelength range of 200 to 780 nm; and (3) recovering 5-bromomethyl-1-benzothiophene from the reactor, wherein the reactor is a flow-type photochemical reactor, and the solvent is one or two or more selected from esters and halogenated hydrocarbons.

[2] The method according to [1], wherein the brominating agent is one or two or more selected from bromine, N-bromocaprolactam, N-bromosuccinimide, 1,3-dibromo-5,5-dimethylhydantoin, a bromine-pyridine complex, and copper (II) bromide.

[3] The method according to [1], wherein the brominating agent is one or two selected from N-bromosuccinimide and 1,3-dibromo-5,5-dimethylhydantoin.

[4] The method according to [1], wherein the brominating agent is 1,3-dibromo-5,5-dimethylhydantoin.

[5] The method according to any one of [1] to [4], wherein the solvent is one or two or more selected from esters.

[6] The method according to any one of [1] to [4], wherein the solvent is one or two selected from methyl acetate and ethyl acetate.

[7] The method according to any one of [1] to [6], wherein a reaction temperature is 5 to 70° C.

Advantageous Effects of Invention

The production method of the present invention is a method for producing Compound A from Compound B with simple operation. The production method of the present invention has the following advantages: (1) the method does not use carbon tetrachloride; (2) thus, the method is safe for human bodies; (3) the method produces less 5-dibromomethyl-1-benzothiophene which is a by-product; (3) therefore, the method does not require a complicated purification step; (5) the method produces Compound A in high yield; (6) the produced Compound A has high purity.

The production method of the present invention is useful as a method for industrially producing Compound A.

REFERENCE SIGNS LIST 1 outer cylinder
2 inner cylinder
3 light source
4 introduction part
5 recovery part
6 reaction tube
7 cylinder

DESCRIPTION OF EMBODIMENTS

The present invention will be described in detail below.

Unless otherwise indicated, "%" used herein means mass %.

The term "halogenated hydrocarbons" means, for example, methylene chloride, chloroform, dichloroethane, trichloroethylene or tetrachloroethylene.

The term "esters" means, for example, methyl acetate, ethyl acetate, propyl acetate, butyl acetate or isoamyl acetate.

Next, the production method of the present invention will be described.

[Production Method 1]

[Formula 1]

[B]  [A]

Compound A can be produced by reacting a brominating agent with Compound B under irradiation with light.

The reaction is carried out using a flow-type photochemical reactor. The production method of the present invention includes the following three steps.

<Step 1> Step of Introducing Compound B, Brominating Agent and Solvent into Reactor This step is a step of introducing Compound B, a brominating agent and a solvent into a reactor.

Examples of step 1 include
(Step 1A) a step of introducing a mixture containing Compound B and a solvent, and a mixture containing a brominating agent and a solvent, separately into a reactor, and mixing the mixtures in the reactor, and
(Step 1B) a step of preparing a mixture containing Compound B, a brominating agent and a solvent, and then introducing the mixture into a reactor.

Preferred examples of step 1 include step 1B.

More preferred examples of step 1 include a step comprising the steps of:
(a) preparing a mixture containing Compound B and a solvent;
(b) preparing a mixture containing a brominating agent and a solvent;
(c) mixing the mixture obtained in (a) with the mixture obtained in (b);
(d) introducing the mixture obtained in (c) into a reactor.

The mixture containing Compound B and a solvent is preferably a solution containing Compound B and a solvent.

The mixture containing a brominating agent and a solvent is preferably a solution containing a brominating agent and a solvent.

The mixture containing Compound B, a brominating agent and a solvent is preferably a solution containing Compound B, a brominating agent and a solvent.

The mixture obtained in (a) is preferably a solution obtained in (a), and the mixture obtained in (b) is preferably a solution obtained in (b).

The mixture obtained in (c) is preferably a solution obtained in (c).

The step of (c) is preferably carried out just before the step of (d).

The solvent used in this reaction is not particularly limited, as long as it is a solvent which does not affect the reaction. Examples of the preferred solvent include one or two or more selected from esters and halogenated hydrocarbons, more preferably one or two or more selected from esters, and further preferably one or two selected from methyl acetate and ethyl acetate.

The amount of solvent to be used is not particularly limited, but the amount of solvent may be 1 to 200 times (v/w) that of Compound B, and is preferably 1 to 5 times (v/w).

Compound B is preferably dissolved.

Examples of the brominating agent used in this reaction are one or two or more selected from bromine, N-bromocaprolactam, N-bromosuccinimide (hereinafter sometimes referred to as "NBS"), 1,3-dibromo-5,5-dimethylhydantoin (hereinafter sometimes referred to as "DBH"), N-bromoacetamide, N-bromophthalimide, N-bromomaleimide, N-bromobenzenesulfonamide, a bromine-pyridine complex and copper(II) bromide, preferably one or two selected from N-bromosuccinimide and 1,3-dibromo-5,5-dimethylhydantoin, and more preferably 1,3-dibromo-5,5-dimethylhydantoin.

The amount of the brominating agent to be used depends on the kind of the brominating agent.

For example, when NBS is used, the amount of NBS to be used may be 0.7 to 1.3 equivalents based on that of Compound B, and is preferably 0.8 to 1.2 equivalents, more preferably 0.9 to 1.2 equivalents, and further preferably 1.0 to 1.2 equivalents.

For example, when DBH is used, the amount of DBH to be used may be 0.35 to 0.65 equivalents based on that of Compound B, and is preferably 0.40 to 0.60 equivalents, more preferably 0.45 to 0.60 equivalents, and further preferably 0.50 to 0.60 equivalents.

When the mixture containing the brominating agent and the solvent is prepared, the preferred solvents are the same as described above.

The amount of solvent to be used is not particularly limited, but may be 5 to 200 times (v/w) that of the brominating agent, and is preferably 10 to 50 times (v/w).

The brominating agent is preferably dissolved.

To set the amount of the brominating agent to be used within the ranges mentioned above based on that of Compound B, it is preferable to adjust the concentration of the brominating agent.

<Step 2> Step of Irradiating Interior of Reactor with Light having Wavelength Range of 200 to 780 nm This step is a step of reacting the brominating agent with Compound B which is introduced into the reactor, under irradiation with light.

The mixture containing Compound B and the brominating agent is irradiated with light. For the irradiation with light, a light source is preferably used.

Examples of the light source include a xenon lamp, sunlight, an ultra-high pressure mercury lamp, a high pressure mercury lamp, a low pressure mercury lamp, a metal halide lamp and an LED (light emitting diode), and preferably a high pressure mercury lamp, a metal halide lamp and an LED.

Light to be irradiated may be any light having a wavelength range of 200 to 780 nm, and is preferably light having a wavelength range of 250 to 500 nm, and more preferably light having a wavelength range of 300 to 450 nm.

The reaction temperature may be 5 to 70° C., and is preferably 20 to 60° C.

The reaction time may be 0.5 to 30 minutes, and is preferably 0.7 to 15 minutes, and more preferably 1 to 5 minutes. The reaction time is the time required to pass through the reactor, since the reaction is carried out by using a flow-type photochemical reactor. To set the reaction time within the ranges mentioned above, it is preferable to adjust the introduction rate.

The reaction time can be determined, for example, from the space volume in which the reaction is carried out, and the introduction rate.

<Step 3> Step of Recovering Compound A from Reactor

This step is a step of recovering Compound A produced by the reaction from the reactor.

Compound A can be isolated from a mixture containing Compound A by any conventional method, such as a concentration, a distillation, an extraction, a crystallization, and/or column chromatography.

When a further reaction is conducted using Compound A in a possible next step, the Compound A may be used with isolation or directly used without isolation in the next step.

The production method of the present invention is carried out using a flow-type photochemical reactor.

Figure 1:
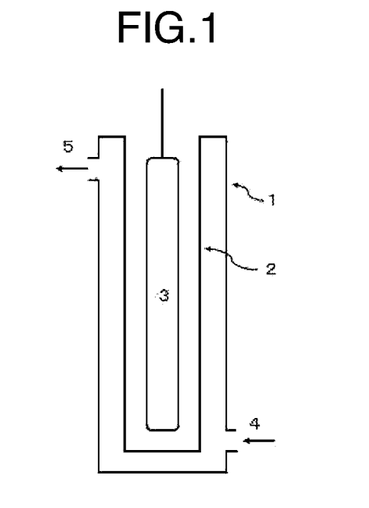
FIG. 1 is a drawing illustrating an aspect of a flow-type photochemical reactor used in the present invention.

An aspect of the flow-type photochemical reactor used in the present invention is shown in FIG. 1.

The flow-type photochemical reactor used in the present invention includes, for example, an outer cylinder, an inner cylinder and a light source.

The outer cylinder is preferably in a tubular form, and has an introduction part and a recovery part.

The inner cylinder is preferably in a transparent tubular form so that light can be transmitted, and has a light source therein.

The space partitioned by the outer cylinder and the inner cylinder is closed, and the reaction is carried out in the closed space.

The mixture containing Compound B and the brominating agent is introduced into the reactor from the introduction part of the outer cylinder, and the reaction is carried out with the irradiation with light, then a mixture containing Compound A is recovered from the recovery part. To make the light irradiated from the light source contribute efficiently to the reaction, the material of the outer cylinder may be selected from materials having a high light-reflection efficiency (such as aluminum). Alternately and/or additionally, a light reflecting material may be provided on the outer side of the outer cylinder.

The sizes of the outer cylinder and the inner cylinder are not particularly limited. It may be set in consideration of the reaction temperature, the reaction time, the introduction rate, and the like.

Figure 2:
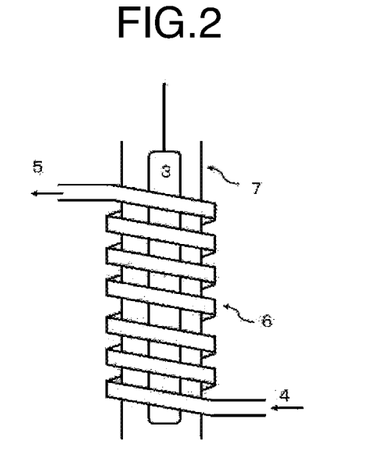
FIG. 2 is a drawing illustrating another aspect of a flow-type photochemical reactor used in the present invention.

Another aspect of the flow-type photochemical reactor used in the present invention is shown in FIG. 2.

The flow-type photochemical reactor used in the present invention includes, for example, a reaction tube, a cylinder and a light source.

The reaction tube is a tube wrapping a cylinder, and preferably transparent so that light can be transmitted. One end of the reaction tube is the introduction part, and the other end is the recovery part.

The cylinder is preferably a transparent cylinder so that light can be transmitted, and has a light source therein.

A mixture containing Compound B and a brominating agent is introduced into the reaction tube, and the reaction is carried out with the irradiation with light, then a mixture containing Compound A is recovered.

The sizes of the reaction tube and the cylinder are not particularly limited. It may be set in consideration of the reaction temperature, the reaction time, the introduction rate, and the like.

Examples of another aspect of the flow-type photochemical reactor for use in the present invention may include a microreactor.

Next, the production method of the present invention will be described in Test Examples, Reference Examples, Examples, Comparative Examples and Production Examples, however, the present invention is not limited by these Examples.

The abbreviations have the following meanings.

Ac: acetyl

AcOEt: ethyl acetate

AcOMe: methyl acetate

DBH: 1,3-dibromo-5,5-dimethylhydantoin eq: equivalent

Et: ethyl

FEP: tetrafluoroethylene-hexafluoropropylene copolymer

HPLC: high-performance liquid chromatography

LED: light emitting diode

Me: methyl

NBS: N-bromosuccinimide

THF: tetrahydrofuran

Unless otherwise stated, the HPLC measurement conditions were as follows.

Detector: ultraviolet absorption spectrophotometer

Measurement Wave length: 230 nm

Column: Symmetry C18 5 μm, inner diameter 4.6× length 150 mm

Column temperature: 40° C.

Mobile phase: 50% acetonitrile buffer solution (0.05 mol/L phosphate buffer solution (pH 7.0))

Flow rate: 1 mL/min

NMR spectra was measured by JNM-AL400-type spectrometer (manufactured by JEOL Ltd.) using tetramethylsilane as an internal standard, and all of the obtained δ values were shown in ppm.

Test Example 1

Compound A was produced from Compound B using a batch-type reaction. The reaction mixture was analyzed by HPLC, and the peak area ratio of each compound was calculated. The results are shown below.

TABLE 1

|  | brominating agent (eq) | solvent | reaction temperature (° C.) | reaction time (min) | peak area ratio (%) | | | |
|---|---|---|---|---|---|---|---|---|
|  |  |  |  |  | [B] | [A] | [C] | [D] |
| Comparative Example 1 | NBS (1.7) | Benzene | 75~80 | 30 | 0.4 | 60 | 22 | 0.3 |
| Comparative Example 2 | NBS (1.7) | CH$_3$CN | 75~80 | 30 | 0.6 | 0.2 | <0.1 | 69 |
| Comparative Example 3 | NBS (1.7) | AcOEt | 75~80 | 30 | 7 | 78 | 1 | 4 |
| Comparative Example 4 | NBS (1.7) | AcOEt | 40~45 | 60 | 0.1 | 71 | 8 | 1 |

In Comparative Examples 1 to 3, the batch-type reactions are carried out using 2,2'-azobis(2-methylpropionitrile) as the radical generator and without the use of light.

In Comparative Example 4, the batch-type reaction is carried out using a high pressure mercury lamp.

When benzene was used as the reaction solvent (Comparative Example 1), a large amount of Compound C was generated.

When acetonitrile was used as the reaction solvent (Comparative Example 2), a large amount of Compound D was generated.

When ethyl acetate was used as the reaction solvent (Comparative Example 3), the peak area ratio of Compound A was 78% and the by-products were less generated.

When ethyl acetate was used as the reaction solvent, and a high pressure mercury lamp was used for the batch-type reaction (Comparative Example 4), the radical generator was not required, and the reaction temperature could be lowered. Further, the peak area ratio of Compound A was 71% and the by-products were less generated.

Previously, in the methods for producing Compound A, carbon tetrachloride has been used as a reaction solvent. However, it has been found that esters can also be used to cause the reaction to proceed. Further, it has been found that when a high pressure mercury lamp is used, the radical generator is not required, the reaction temperature can be lowered, and the by-products are less generated.

Test Example 2

Compound A was produced from Compound B using a flow-type reaction. The reaction mixture was analyzed by HPLC, and the peak area ratio of each compound was calculated. The results are shown below.

TABLE 2

[Reaction scheme: Compound [B] (5-methylbenzothiophene) → Compound [A] (5-(bromomethyl)benzothiophene)]

[Byproducts: [C] 5-(dibromomethyl)benzothiophene, [D] 3-bromo-5-methylbenzothiophene]

| | light source | brominating agent (eq) | solvent | reaction temperature (° C.) | reaction time (min) | peak area ratio (%) | | | |
|---|---|---|---|---|---|---|---|---|---|
| | | | | | | [B] | [A] | [C] | [D] |
| Example 1 | high pressure mercury lamp | NBS (1.1) | AcOEt | 30 | 2 | 1 | 90 | 3 | 1 |
| Example 2 | high pressure mercury lamp | DBH (0.55) | AcOEt | 10 | 1 | 11 | 80 | 1 | 3 |
| Example 3 | high pressure mercury lamp | DBH (0.55) | AcOEt | 30 | 2 | 5 | 88 | 2 | 1 |
| Example 4 | high pressure mercury lamp | DBH (0.55) | AcOEt | 40 | 1 | 9 | 86 | 2 | 1 |
| Example 5 | high pressure mercury lamp | DBH (0.55) | AcOMe | 30 | 2 | 8 | 85 | 1 | 2 |
| Example 6 | high pressure mercury lamp | DBH (0.55) | AcOMe | 40 | 1 | 8 | 85 | 3 | 1 |
| Example 7 | high pressure mercury lamp | DBH (0.55) | $CH_2Cl_2$ | 30 | 1 | 10 | 81 | 2 | 3 |
| Comparative Example 5 | high pressure mercury lamp | DBH (0.55) | THF | 15~20 | 1 | 96 | 2 | <0.1 | 1 |

In Example 1, the reaction is carried out using ethyl acetate as the reaction solvent and NBS as the brominating agent.

In Examples 2 to 7, the reaction is carried out using ethyl acetate or methyl acetate as the reaction solvent and DBH as the brominating agent.

In Comparative Example 5, the reaction is carried out using THF as the reaction solvent and DBH as the brominating agent.

All of these reactions are flow-type photochemical reactions using a high-pressure mercury lamp.

When THF was used as the reaction solvent (Comparative Example 5), the reaction did not proceed.

On the other hand, in the reactions of Examples 1 to 7, the peak area ratio of Compound A was 80% or more, and the by-products were less generated. Further, the reaction temperature could be lowered and the reaction time could be greatly shortened, compared with the batch-type reaction (Comparative Examples 1 to 4).

The flow-type photochemical reaction was excellent as a method for industrially producing Compound A.

Test Example 3

Compound A was produced from Compound B using a flow-type reaction. The reaction mixture was analyzed by HPLC, and the peak area ratio of each compound was calculated. The results are shown below.

TABLE 3

| | light source | brominating agent (eq) | solvent | reaction temperature (° C.) | reaction time (min) | peak area ratio (%) [B] | [A] | [C] | [D] |
|---|---|---|---|---|---|---|---|---|---|
| Example 8 | LED (300 nm) | DBH (0.55) | AcOEt | 20 | 1 | 12 | 79 | 2 | 2 |
| Example 9 | LED (365 nm) | DBH (0.55) | AcOEt | 20 | 1 | 10 | 84 | 2 | 1 |
| Example 10 | LED (405 nm) | DBH (0.55) | AcOEt | 20 | 1 | 6 | 86 | 2 | 1 |

In Examples 8 to 10, flow-type photochemical reactions are carried out using an LED as a light source.

In all of the Examples 8 to 10, the peak area ratio of Compound A was 79% or more and the by-products were less generated.

The flow-type photochemical reaction was excellent as a method for industrially producing Compound A.

Example 1

[Formula 2]

A solution of 1.1 g of 5-methyl-1-benzothiophene (Compound B) in 3.3 mL of ethyl acetate was prepared (solution I). Separately, a solution of 0.66 g of NBS in 25 mL of ethyl acetate was prepared (solution II). The solutions I and II were each fed by a syringe pump to an in-line mixer connected to a FEP tube having an inner diameter of 0.5 mm, where the flow rates of the solutions I and II were adjusted so that the amount of NBS was 1.1 equivalents based on that of Compound B. After mixing the solutions I and II in the in-line mixer, the FEP tube was irradiated with a high pressure mercury lamp (UM-102, manufactured by Ushio Inc.). The average residence time the solution takes to pass through the section irradiated with the high-pressure mercury lamp was set to 2 minutes. Further, the in-line mixer and a high pressure mercury lamp wrapped with the reaction tube were immersed in a water bath and the water temperature was held at 30° C. The obtained reaction solution was measured by HPLC, and it was determined that the peak area ratio of Compound A was 90%. The peak area ratios of Compounds B, C and D are shown in Table 2.

Example 2

[Formula 3]

A solution of 2.00 g of 5-methyl-1-benzothiophene (Compound B) in 6 mL of ethyl acetate was prepared (solution I). Separately, a solution of 3.18 g of DBH in 90 mL of ethyl acetate was prepared (solution II). The solutions I and II were each fed by a syringe pump to an in-line mixer connected to a FEP tube having an inner diameter of 0.5 mm, where the flow rates of the solutions I and II were adjusted so that the amount of DBH was 0.55 equivalents based on that of Compound B. After mixing the solutions I and II in the in-line mixer, the FEP tube was irradiated with a high pressure mercury lamp (UM-102, manufactured by Ushio Inc.). The average residence time the solution takes to pass through the section irradiated with the high-pressure mercury lamp was set to 1 minute. Further, the in-line mixer and a high pressure mercury lamp wrapped with the reaction tube were immersed in a water bath and the water temperature was held at 10° C. The obtained reaction solution was measured by HPLC, and it was determined that the peak area ratio of Compound A was 80%. The peak area ratios of Compounds B, C and D are shown in Table 2.

Example 3

The reaction was carried out in the same manner as in Example 2, except that the average residence time was set to 2 minutes and the water temperature of water bath was held at 30° C.

The obtained reaction solution was measured by HPLC, and it was determined that the peak area ratio of Compound A was 88%. The peak area ratios of Compounds B, C and D are shown in Table 2.

Example 4

The reaction was carried out in the same manner as in Example 2, except that the water temperature of water bath was held at 40° C.

The obtained reaction solution was measured by HPLC, and it was determined that the peak area ratio of Compound A was 86%. The peak area ratios of Compounds B, C and D are shown in Table 2.

Example 5

A solution of 3.00 g of 5-methyl-1-benzothiophene (Compound B) in 4.5 mL of ethyl acetate was prepared (solution I). Separately, a solution of 1.06 g of DBH in 14 mL of methyl acetate was prepared (solution II). The solutions I and II were each fed by a syringe pump to an in-line mixer connected to a FEP tube having an inner diameter of 0.5 mm, where the flow rates of the solutions I and II were adjusted so that the amount of DBH was 0.55 equivalents based on that of Compound B. After mixing the solutions I and II in the in-line mixer, the FEP tube was irradiated with a high pressure mercury lamp (UM-102, manufactured by Ushio Inc.). The average residence time the solution takes to pass through the section irradiated with the high-pressure mercury lamp was set to 2 minutes. Further, the in-line mixer and a high pressure mercury lamp wrapped with the reaction tube were immersed in a water bath and the water temperature was held at 30° C. The obtained reaction solution was measured by HPLC, and it was determined that the peak area ratio of Compound A was 85%. The peak area ratios of Compounds B, C and D are shown in Table 2.

Example 6

The reaction was carried out in the same manner as in Example 5, except that the average residence time was set to 1 minute and the water temperature of water bath was held at 40° C.

The obtained reaction solution was measured by HPLC, and it was determined that the peak area ratio of Compound A was 85%. The peak area ratios of Compounds B, C and D are shown in Table 2.

Example 7

A solution of 0.50 g of 5-methyl-1-benzothiophene (Compound B) in 1.5 mL of methylene chloride was prepared (solution I). Separately, a solution of 0.53 g of DBH in 15 mL of methylene chloride was prepared (solution II). The solutions I and II were each fed by a syringe pump to an in-line mixer connected to a FEP tube having an inner diameter of 0.5 mm, where the flow rates of the solutions I and II were adjusted so that the amount of DBH was 0.55 equivalents based on that of Compound B. After mixing the solutions I and II in the in-line mixer, the FEP tube was irradiated with a high pressure mercury lamp (UM-102, manufactured by Ushio Inc.). The average residence time the solution takes to pass through the section irradiated with the high-pressure mercury lamp was set to 1 minute. Further, the in-line mixer and a high pressure mercury lamp wrapped with the reaction tube were immersed in a water bath and the water temperature was held at 30° C. The obtained reaction solution was measured by HPLC, and it was determined that the peak area ratio of Compound A was 81%. The peak area ratios of Compounds B, C and D are shown in Table 2.

Example 8

A solution of 0.40 g of 5-methyl-1-benzothiophene and 0.42 g of DBH in 13 mL of ethyl acetate was prepared. The resulting solution was fed by a syringe pump to a quartz flow channel plate forming a rectangular flow channel having a depth of 1.0 mm and a width of 1.0 mm. The quartz flow channel plate was irradiated with light having the wavelength of 300 nm using an LED lamp (300 nm LED 3×3 array, manufactured by Nikkiso Co. Ltd.) at room temperature. The average residence time the solution takes to pass through the section irradiated with the LED lamp was set to 1 minute. The obtained reaction solution was measured by HPLC, and it was determined that the peak area ratio of Compound A was 79%. The peak area ratios of Compounds B, C and D are shown in Table 3.

Example 9

The reaction was carried out in the same manner as in Example 8, except that the irradiation was conducted with light having the wavelength of 365 nm using an LED lamp (MZeroLED, manufactured by Integration Technology Co., Ltd.) as a light source.

The obtained reaction solution was measured by HPLC, and it was determined that the peak area ratio of Compound A was 84%. The peak area ratios of Compounds B, C and D are shown in Table 3.

Example 10

The reaction was carried out in the same manner as in Example 8, except that the irradiation was conducted with light having the wavelength of 405 nm using an LED lamp (233A, manufactured by MATSUO SANGYO CO., LTD.) as a light source.

The obtained reaction solution was measured by HPLC, and it was determined that the peak area ratio of Compound A was 86%. The peak area ratios of Compounds B, C and D are shown in Table 3.

Comparative Example 1

To a mixture of 2.04 g of NBS and 22 mg of 2,2'-azobis (2-methylpropionitrile) in 15 mL of benzene, a solution of 1.00 g of 5-methyl-1-benzothiophene and 22 mg of 2,2'-azobis(2-methylpropionitrile) in 9 mL of benzene was added dropwise at 80° C. over 30 minutes, and the resulting mixture was stirred for 30 minutes at the same temperature. The obtained reaction solution was measured by HPLC, and it was determined that the peak area ratio of Compound A was 60%. The peak area ratios of Compounds B, C and D are shown in Table 1.

Comparative Example 2

To a mixture of 410 mg of NBS and 4 mg of 2,2'-azobis (2-methylpropionitrile) in 3 mL of acetonitrile, a solution of 200 mg of 5-methyl-1-benzothiophene and 4 mg of 2,2'-azobis (2-methylpropionitrile) in 3.6 mL of acetonitrile was added dropwise at 80° C. over 30 minutes, and the resulting mixture was stirred for 30 minutes at the same temperature.

The obtained reaction solution was measured by HPLC, and it was determined that the peak area ratio of Compound A was 0.2%. The peak area ratios of Compounds B, C and D are shown in Table 1.

Comparative Example 3

To a 10 mL mixture of 200 mg of 5-methyl-1-benzothiophene and 410 mg of NBS in ethyl acetate, 9 mg of 2,2'-azobis (2-methylpropionitrile) was added. The obtained mixture was stirred under reflux for 30 minutes. The obtained reaction solution was measured by HPLC, and it was determined that the peak area ratio of Compound A was 78%. The peak area ratios of Compounds B, C and D are shown in Table 1.

Comparative Example 4

A 10 mL mixture of 100 mg of 5-methyl-1-benzothiophene and 200 mg of NBS in ethyl acetate was stirred at 40 to 45° C. for 60 minutes while being irradiated with a high-pressure mercury lamp (UM-102, manufactured by Ushio Inc.). The obtained reaction solution was measured by HPLC, and it was determined that the peak area ratio of Compound A was 71%. The peak area ratios of Compounds B, C and D are shown in Table 1.

Comparative Example 5

A solution of 600 mg of 5-methyl-1-benzothiophene and 640 mg of DBH in 6 mL of THF was prepared. The obtained solution was fed by a syringe pump to a FEP tube having an inner diameter of 0.5 mm, and then irradiated with a high pressure mercury lamp (UM-102, manufactured by Ushio Inc.). The average residence time the solution takes to pass through the section irradiated with the high-pressure mercury lamp was set to 1 minute. Further, a high pressure mercury lamp wrapped with the reaction tube were immersed in a water bath and the water temperature was held at 15 to 20° C. The obtained reaction solution was measured by HPLC, and it was determined that the peak area ratio of Compound A was 2%. The peak area ratios of Compounds B, C and D are shown in Table 2.

Reference Example 1

[Formula 4]

3-Bromo-5-methyl-1-benzothiophene was obtained by using the method described in International Publication No. WO2012/073888 pamphlet.

Reference Example 2

[Formula 5]

The mixture containing Compound A and Compound C obtained by the same method as in Comparative Example 1 was purified and separated by silica gel column chromatography to obtain 5-dibromomethyl-1-benzothiophene as a red-brown solid.

$^1$H-NMR (CDCl$_3$) δ: 7.45-7.52 (2H, m), 7.58 (1H, d, J=8.3 Hz), 7.87 (1H, d, J=8.5 Hz), 8.01 (1H, d, J=5.6 Hz), 8.32 (1H, s)

Production Example 1

[Formula 6]

By the same method as in Example 6, Compound A was produced from 10.0 g of 5-methyl-1-benzothiophene. The resulting reaction solution was subjected to distillation of the solvent under reduced pressure, and toluene and water was added thereto. The organic layer was separated, and washed with saturated aqueous sodium bicarbonate solution. The organic layer was separated, and the solvent was distilled off under reduced pressure. To the resulting residue, 25 mL of water, 25 mL of toluene, 5.59 g of potassium carbonate, 5.27 g of cyan potassium and 650 mg of tetrabutylammonium bromide were added, and stirred at 60° C. for 90 minutes. The reaction mixture was cooled to room temperature, the organic layer was separated and washed with water. The organic layer was separated, the solvent was distilled off under reduced pressure to obtain (1-benzothiophen-5-yl) acetonitrile.

Production Example 2

[Formula 7]

-continued

5

To (1-benzothiophen-5-yl) acetonitrile obtained in Production Example 1, 15 mL of water, 10 mL of propylene glycol and 6.48 g of sodium hydroxide were added, and the mixture was stirred at 90° C. for 3 hours. The reaction mixture was cooled to room temperature, water was added thereto, and the aqueous layer was separated. The obtained aqueous layer was washed with toluene, 0.5 g of the activated carbon was added thereto, and the mixture was stirred at 50° C. for 10 minutes. The insoluble material was filtered off, and then the residue was washed with water. The filtrate and the washings were combined, and 40 mL of ethanol, 6 mL of ethyl acetate, 15 mL of water and 14 mL of hydrochloric acid were added thereto. The mixture was warmed to 50° C., and then cooled to 5° C. To the resulting mixture, water was added, and the solid was collected by filtration to give 9.34 g of (1-benzothiophen-5-yl) acetic acid as the pale yellowish white solid.

$^1$H-NMR (CDCl$_3$) δ: 3.77 (2H, s), 7.24-7.32 (1H, m), 7.30 (1H, d, J=5.5 Hz), 7.44 (1H, d, J=5.5 Hz), 7.72-7.75 (1H, m), 7.84 (1H, d, J=8.3 Hz)

Production Example 3

[Formula 8]

1-(3-(2-(1-benzothiophen-5-yl)ethoxy)propyl)azetidin-3-ol was obtained using 1-benzothiophen-5-acetic acid, according to the methods described in JP 2012-046499 A and International Publication No. WO2006/104088 pamphlet.

INDUSTRIAL APPLICABILITY

The production method of the present invention is useful as a method for industrially producing 5-bromomethyl-1-benzothiophene which is useful as a production intermediate for pharmaceuticals.

The invention claimed is:

1. A method for producing 5-bromomethyl-1-benzothiophene, comprising:
    (1) introducing 5-methyl-1-benzothiophene, a brominating agent and a solvent into a reactor to obtain a reaction mixture;
    (2) irradiating the interior of the reactor with light having a wavelength range of 200 to 780 nm; and
    (3) recovering the reaction mixture comprising 5-bromomethyl-1-benzothiophene from the reactor, wherein the 5-bromomethyl-1-benzothiophene is directly used without isolation in a next cyanation step,
  wherein
  the reactor is a flow-type photochemical reactor,
  the solvent is at least one selected from the group consisting of methyl acetate and ethyl acetate,
  a peak area ratio of 5-bromomethyl-1-benzothiophene in the reaction mixture is 79% or more,
  a peak area ratio of 5-dibromomethyl-1-benzothiophene in the reaction mixture is 3% or less, and
  a peak area ratio of 3-bromo-5-methyl-1-benzothiophene in the reaction mixture is 3% or less.

2. The method according to claim 1, wherein the brominating agent is at least one selected from the group consisting of bromine, N-bromocaprolactam, N-bromosuccinimide, 1,3-dibromo-5,5-dimethylhydantoin, a bromine-pyridine complex and copper(II) bromide.

3. The method according to claim 1, wherein the brominating agent is at least one selected from the group consisting of N-bromosuccinimide and 1,3-dibromo-5,5-dimethylhydantoin.

4. The method according to claim 1, wherein the brominating agent is 1,3-dibromo-5,5-dimethylhydantoin.

5. The method according to claim 1, wherein a reaction temperature is from 5 to 70° C.

* * * * *